United States Patent [19]
Rice

[11] Patent Number: 6,008,427
[45] Date of Patent: Dec. 28, 1999

[54] TOTAL ISOMERIZATION PROCESS WITH ENHANCED HEAT INTEGRATION

[75] Inventor: Lynn H. Rice, Arlington Heights, Ill.

[73] Assignee: UOP LLC, Des Plaines, Ill.

[21] Appl. No.: 09/072,007

[22] Filed: May 4, 1998

[51] Int. Cl.$^6$ ................................. C07C 5/13; C07C 7/12
[52] U.S. Cl. .................... 585/737; 585/738; 585/739; 585/750; 585/820; 585/826
[58] Field of Search ..................................... 585/737, 738, 585/739, 750, 820, 826

[56] References Cited

U.S. PATENT DOCUMENTS

| | | | |
|---|---|---|---|
| 4,210,771 | 7/1980 | Holcombe | 585/701 |
| 4,709,117 | 11/1987 | Gray, Jr. | 585/738 |
| 4,929,799 | 5/1990 | Holcombe et al. | 585/737 |
| 5,036,035 | 7/1991 | Baba et al. | 502/221 |
| 5,120,898 | 6/1992 | Baba et al. | 585/750 |

*Primary Examiner*—Walter D. Griffin
*Assistant Examiner*—In Suk Bullock
*Attorney, Agent, or Firm*—Thomas K. McBride; Frank S. Molinaro; Maryann Maas

[57] ABSTRACT

A method providing enhanced heat integration in isomerization processes having an isomerization reactor operating at a temperature less than about 232° C. (450° F.) and an adsorption zone operating at a temperature greater than about 260° C. (500° F.) has been developed. The method begins with flowing a fresh feed stream containing normal and non-normal hydrocarbons to either the isomerization reactor or the adsorption zone. A variable mass flow desorption effluent containing at least normal hydrocarbons is flowed to the isomerization reactor to form a reactor effluent containing normal hydrocarbons and isomerized non-normal hydrocarbons. The reactor effluent is cooled and separated into an adsorber feed stream and a hydrogen purge gas which are each conducted to an adsorption zone. In the adsorption zone, the normal hydrocarbons are adsorbed and the non-normal hydrocarbons are withdrawn and collected. The normal hydrocarbons are then desorbed from the adsorption zone using the hydrogen purge gas to produce the desorption effluent. The adsorber feed stream, the hydrogen purge gas, or both, are heat exchanged with the desorption effluent so that the desorption effluent flowing into the reactor is at about the operating temperature of the reactor and the adsorber feed stream, the hydrogen purge gas, or both, are partially heated. The partially heated adsorber feed stream, hydrogen purge gas, or both, are further heated using a controlled variable heat providing stream such as a steam or hot oil stream so that the temperature of the adsorber feed stream and hydrogen purge gas flowing into the adsorption zone are closer to the operating temperature of the adsorption zone.

24 Claims, 1 Drawing Sheet

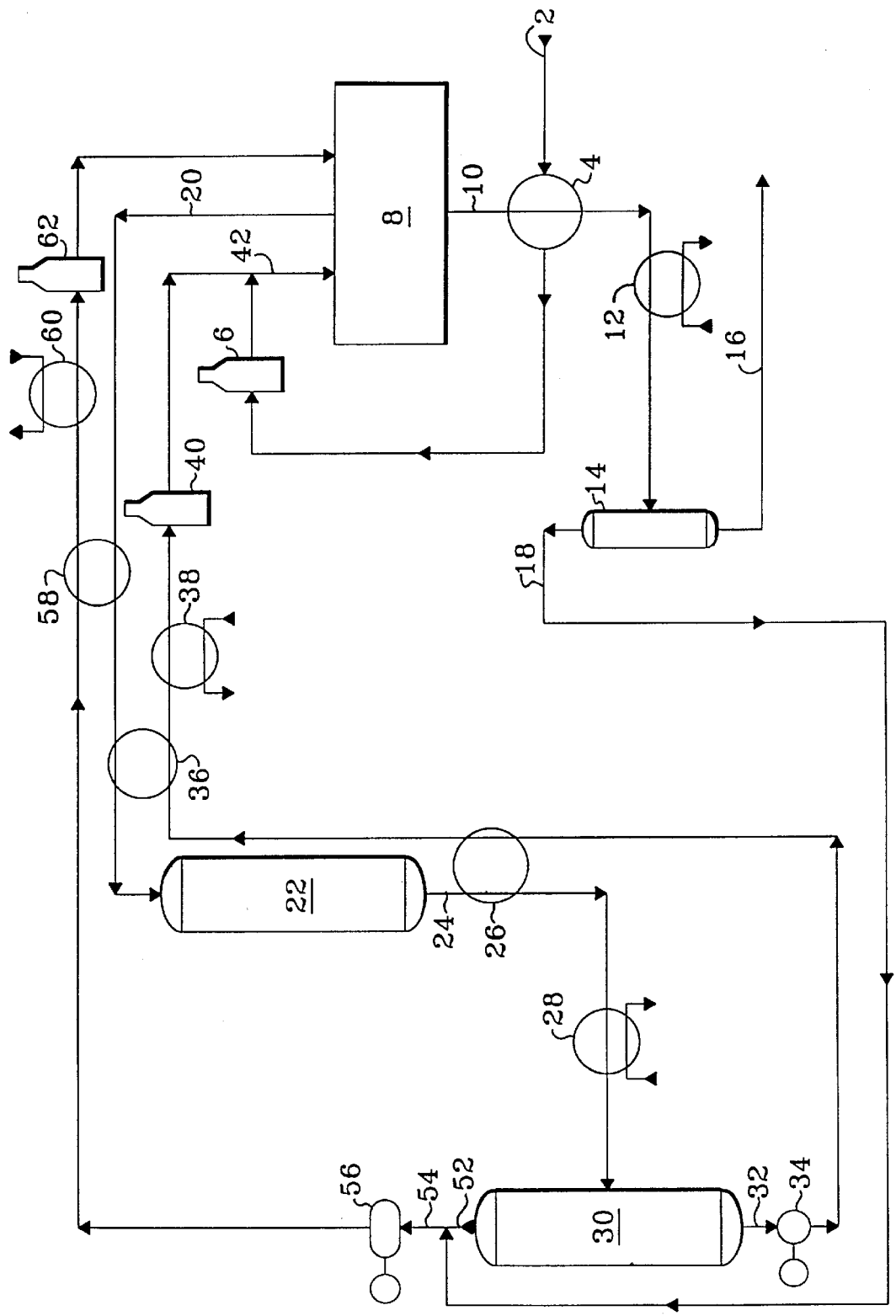

TOTAL ISOMERIZATION PROCESS WITH ENHANCED HEAT INTEGRATION

BACKGROUND OF THE INVENTION

Hydrocarbon isomerization processes are widely used to convert normal hydrocarbons to more valuable non-normal hydrocarbons. The more valuable non-normal hydrocarbons may be used as gasoline blending components to boost the octane number of the gasoline or as intermediates for such oxygenate products as methyl tertiary butyl ether, ethyl tertiary butyl ether, and tertiary amyl ethyl ether. One class of vapor phase hydrocarbon isomerization processes uses adsorption technology to remove non-isomerized normal hydrocarbons from the isomerization reactor effluent. The adsorbed normal hydrocarbons are desorbed using hydrogen and recycled to the isomerization reactor. The overall production of the process is enhanced by keeping reactants in circulation within the process until the desired products are formed. Typically this class of isomerization processes is referred to as total isomerization processes, or TIP. Detailed descriptions of variations of this isomerization technique may be found in Crusher, N. A. In *Handbook of Petroleum Refining Processes* $2^{nd}$ ed.; Meyers, R. A. Ed.; McGraw-Hill: New York, 1997; pp 9.29–9.39, U.S. Pat. No. 4,210,771, U.S. Pat. No. 4,709,117, and U.S. Pat. No. 4,929,799 which are all incorporated by reference.

As with most processes, significant operational costs to be considered in total isomerization processes include the cost of utilities. Innovations to reduce the utilities' costs are continuously sought and those that are successful can greatly improve the economics of the process. Heat integration is one technique used to reduce utilities' costs. U.S. Pat. No. 4,210,771 discloses using specific heat integration in an isomerization process such as described above. The reference discloses a variable fresh feed that is combined with the desorption effluent from an adsorbent bed used to adsorb normal hydrocarbons. The combined streams are then flowed to an isomerization reactor. Before the adsorbed normal hydrocarbons elute from the adsorbent bed, an adsorption effluent containing non-normal hydrocarbon product is withdrawn from the adsorbent bed. The adsorption effluent is heat exchanged with the fresh feed to partially heat the fresh feed before it is combined with the desorption effluent and introduced into the reactor.

Utility consumption and therefore cost has also been reduced by new catalysts developed for use in the isomerization reactor; see U.S. Pat. No. 5,036,035 and U.S. Pat. No. 5,120,898 both of which are incorporated by reference. Traditional temperatures in the isomerization reactor have been in the range of 245° C. to 370° C., but newer catalysts are efficient at significantly lower temperatures such as from about 70° C. to about 250° C.; see U.S. Pat. No. 5,120,898, incorporated by reference. However, current adsorbents used in the adsorption zone require that the adsorption zone continue to be operated at the higher temperatures in order to prevent capillary condensation in the adsorbent pores.

The newer catalysts and the resulting temperature variation between the adsorption zone and the isomerization reactor have provided the opportunity for enhanced heat integration. The temperature of the stream carrying normal hydrocarbons from the adsorption zone to the isomerization reactor, the desorption effluent, must be reduced from the operating temperature of the adsorption zone to the operating temperature of the isomerization reactor while at the same time, the reactor effluent is cooled and separated to form an adsorber feed stream and a hydrogen purge gas each of which must be increased to that of the adsorption zone. The present invention reduces the utility costs of the overall process through heat exchanging the adsorber feed and/or the hydrogen purge gas with the desorption effluent. However, because the desorption effluent is not a constant mass flow stream, traditional heat exchanging techniques are insufficient. The present invention requires traditional heat exchanging techniques to be used in conjunction with a variable steam or hot oil flow or in conjunction with a surge drum.

SUMMARY OF THE INVENTION

The purpose of the invention is to provide enhanced heat integration in isomerization processes having an isomerization reactor operating at a temperature less than about 232° C. (450° F.) and an adsorption zone operating at a temperature greater than about 260° C. (500° F.). A hydrocarbon-enriched stream, a hydrogen-enriched stream, or both, are separately heat exchanged with a desorption effluent having a variable mass flow so that the desorption effluent flowing into the isomerization reactor is at about the operating temperature of the reactor. The hydrocarbon-enriched stream is then flowed to the adsorption zone to adsorb the normal hydrocarbons and collect the non-normal hydrocarbons. The normal hydrocarbons are desorbed from the adsorption zone using the hydrogen-enriched stream to produce the desorption effluent.

One embodiment of the invention begins with flowing a fresh feed stream containing normal and non-normal hydrocarbons to either the isomerization reactor or the adsorption zone. A variable mass flow desorption effluent containing at least normal hydrocarbons is flowed to the isomerization reactor containing an isomerization catalyst and operating at 232° C. (450° F.) or less to form a reactor effluent containing normal hydrocarbons and isomerized non-normal hydrocarbons. The reactor effluent is cooled and separated into an adsorber feed stream and a hydrogen purge gas which are each conducted to an adsorption zone operating at 260° C. (500° F.) or greater and containing an adsorbent capable of adsorbing the normal hydrocarbons. In the adsorption zone, the normal hydrocarbons are adsorbed and the non-normal hydrocarbons are withdrawn and collected. The normal hydrocarbons are then desorbed from the adsorption zone using the hydrogen purge gas to produce the desorption effluent. The adsorber feed stream, the hydrogen purge gas, or both, are heat exchanged with the desorption effluent so that the desorption effluent flowing into the reactor is at about the operating temperature of the reactor and the adsorber feed stream, the hydrogen purge gas, or both, are partially heated. The partially heated adsorber feed stream, hydrogen purge gas, or both, are further heated using a controlled variable heat-providing stream such as a steam or hot oil stream so that the temperature of the adsorber feed stream and hydrogen purge gas flowing into the adsorption zone are closer to the operating temperature of the adsorption zone.

Another embodiment of the invention is one where the desorption effluent, which may vary in mass flow over the course of an adsorption-desorption cycle of the adsorption zone, is conducted to a surge drum to provide a constant mass flow desorption effluent. The adsorber feed stream, hydrogen purge gas, or both, are heat exchanged with the constant mass flow desorption effluent from the surge drum so that the desorption effluent flowing into the reactor is at about the operating temperature of the reactor and the adsorber feed stream, hydrogen purge gas, or both, are partially heated.

BRIEF DESCRIPTION OF THE DRAWING

The drawing is a schematic representation of a generic total isomerization process modified and operated in accordance with the process of this invention. The drawing has been simplified by the deletion of a large number of pieces of apparatus customarily employed on processes of this nature which are not specifically required to illustrate the performance of the present invention.

DETAILED DESCRIPTION OF THE INVENTION

The invention is a total isomerization process having enhanced heat integration and therefore lower operating costs as compared to traditional total isomerization processes. As discussed above, the total isomerization process contains two main sections, the isomerization reactor and the adsorption zone. The fresh feed to the process is usually preheated and may be fed either to the isomerization reactor, termed the "reactor-lead" embodiment, or to the adsorption zone, termed the "adsorber-lead" embodiment. The reactor-lead embodiment is preferred when the fresh feed contains a significant amount of normal hydrocarbons, such as greater than 25 mole percent. The adsorber-lead embodiment is preferred when the fresh feed contains an appreciable amount of non-normal hydrocarbons. Reactor-lead and adsorber-lead operations are well understood in the art and are explained in detail in U.S. Pat. No. 4,929,799 which is incorporated by reference. A typical application of the total isomerization process is to isomerize normal hydrocarbons containing from about 4 to about 7 carbon atoms to form the corresponding isomeric non-normal hydrocarbons, and fresh feeds for this typical application are frequently obtained from refinery distillation operations.

The isomerization reactor, which may be one or more serially connected individual reactors, contains an isomerization catalyst that is effective for the isomerization of normal hydrocarbons to non-normal hydrocarbons. However, to realize the benefit of the invention, the isomerization reactor must be operated at a temperature of about 232° C. (450° F.) or less. Various traditional catalysts may have insufficient activity at this low temperature, but newly developed catalysts are effective and therefore preferred. Suitable catalysts include solid strong acid catalysts where sulfate ($SO_4$) and at least one member selected from Group VIII metals are supported on a support consisting of hydroxides and oxides of Group IV metals and Group III metals and mixtures thereof, with the catalyst being calcined and stabilized. These catalysts are described in detail in U.S. Pat. No. 5,036,035 and U.S. Pat. No. 5,120,898 which are both incorporated herein by reference. As hydrocarbons enter the isomerization reactor, whether from a desorption effluent (discussed below) or a combination of desorption effluent and fresh feed, normal hydrocarbons contact the catalyst and a portion of the normal hydrocarbons are isomerized to form non-normal hydrocarbons. Since the isomerization of hydrocarbons is an equilibrium-limited reaction, a portion of the normal hydrocarbon will not be isomerized and will exit the reactor in the reactor effluent. Therefore, the reactor effluent will contain at least hydrogen, normal hydrocarbons, and isomerized non-normal hydrocarbons, with the normal and non-normal hydrocarbons preferably near equilibrium proportions. The reactor effluent will exit the reactor at the operating temperature of the reactor, 232° C. (450° F.) or less.

The reactor effluent is cooled and separated prior to reaching the adsorption zone using common separation techniques such as flashing in a separator drum to separate a hydrogen-enriched stream from a hydrocarbon-enriched stream. The hydrocarbon-enriched stream is used as the adsorber feed, and the hydrogen enriched stream is used as the desorbent or purge gas. The hydrogen-enriched stream contains mainly hydrogen, but if light hydrocarbons are present in the feed, the hydrogen enriched stream may also contain hydrocarbons having from one to about three carbon atoms. The hydrocarbon stream contains mainly hydrocarbons having four or more carbon atoms as well as dissolved hydrogen. Each stream is then flowed, after heat exchanging with the adsorption effluent, reactor effluent, and desorption effluent, or all three, in the vapor state to the adsorption zone. The design and operation of the adsorption zone is well known in the art and is only outlined briefly here.

The adsorber feed containing normal and non-normal hydrocarbons in the vapor state is passed at superatmospheric pressure periodically in sequence through each of a plurality of fixed adsorber beds, e.g., four as described in U.S. Pat. No. 3,700,589 or three as described in U.S. Pat. No. 3,770,621, of an adsorption zone with each bed containing zeolitic molecular sieve adsorbent. The cited United States Patent No. patents are incorporated by reference herein. Preferably, the adsorbents have effective pore diameters of substantially 5 Angstroms. In a four-bed system, each of the beds cyclically undergoes the stages of:

A-1 adsorption-fill wherein the vapor in the bed void space consists principally of hydrogen purge gas with the incoming adsorber feed forcing the hydrogen purge gas from the bed void space and out of the bed without substantial intermixing of the hydrogen purge gas with the non-adsorbed adsorber feed. The term "bed void space" for purposes of this description means any space in the bed not occupied by solid material except the intracrystalline cavities of the zeolite crystals. The pores within any binder material which may be used to form agglomerates of the zeolite crystals is considered to be bed void space;

A-2 adsorption wherein the adsorber feed is cocurrently passed through the bed and the normal hydrocarbons of the adsorber feed are selectively adsorbed into the internal cavities of the crystalline zeolitic adsorbent and the nonadsorbed hydrocarbons of the adsorber feed are removed from the bed as an adsorption effluent having a greatly reduced content of non-normal hydrocarbons;

D-1 void space purging wherein the bed loaded with normal hydrocarbons to the extent that the stoichiometric point of the mass transfer zone thereof has passed between 85 and 97 percent of the length of the bed and containing in the bed void space a mixture of normal and non-normal hydrocarbons in essentially the adsorber feed proportions, is purged countercurrently, with respect to the direction of A-2 adsorption by passing a stream of hydrogen purge gas through the bed in sufficient quantity to remove the bed void space adsorber feed vapors but not more than that which produces about 50 mole percent, preferably not more than 40 mole percent, of adsorbed normal hydrocarbons in the bed effluent; and D-2 purge desorption wherein the selectively adsorbed normal hydrocarbons are desorbed to form a desorption effluent by passing a hydrogen purge gas countercurrently with respect to A-2 adsorption through the bed until a major proportion of adsorbed normal hydrocarbons has been desorbed and the bed void space vapors consist principally of hydrogen purge gas. The hydrogen purge gas may be a hydrogen recycle stream which contains light hydrocarbons in addition to the hydrogen.

The zeolitic molecular sieve employed in the adsorption beds must be capable of selectively adsorbing the normal hydrocarbons of the adsorber feed using molecular size and configuration as the criterion. Such a molecular sieve should, therefore, have an apparent pore diameter of less than about 6 Angstroms and greater than about 4 Angstroms. A particularly suitable zeolite of this type is zeolite A, described in U.S. Pat. No. 2,883,243, which in several of its divalent exchanged forms, notably the calcium cation form, has an apparent pore diameter of about 5 Angstroms and has a very large capacity for adsorbing normal hydrocarbons. Other suitable molecular sieves include zeolite R, U.S. Pat. No. 3,030,181, zeolite T, U.S. Pat. No. 2,950,952, and the naturally occurring, zeolitic molecular sieves chabazite and erionite. The cited United States Patent No. patents are incorporated herein by reference.

For the adsorbents to function properly, the hydrocarbons must be maintained in the vapor state and the adsorption zone must be operated at a temperature above about 260° C. (500° F.), preferably within the range of about 260° C. (500° F.) to about 343° C. (650° F.) with the normal operating pressure of the adsorption zone being in the range of about 200 psig to about 300 psig and preferably about 250 psig. However, the highest temperature the hydrogen purge gas and the adsorber feed stream can achieve is 232° C. (450° F.) after heat exchange with the reactor effluent, so they must be heated to the operating temperature of the adsorption zone. A fired heater may simply be installed to heat the hydrogen purge gas and the adsorber feed stream to the temperature of the adsorption zone, but the present invention provides a more economic and utility conserving solution. The adsorber feed, the hydrogen purge gas, or both, are heat exchanged with the desorption effluent prior to being flowed to the adsorption zone. The desorption effluent exiting the adsorption zone will be at the operating temperature of the adsorption zone, above about 260° C. (500° F.), and must be reduced to the operating temperature of the isomerization reactor, less than about 232° C. (450° F.) while at the same time the adsorber feed and the hydrogen purge gas require heat to increase their temperatures from that of the isomerization reactor closer to the temperature of the adsorption zone. Therefore, the excess heat of the desorption effluent is used to heat the adsorber feed, the hydrogen purge gas, or both, via heat exchange.

However, the desorption effluent is not a constant stream. The space velocity or mass flow of the desorption effluent varies by as much as 50 percent over an adsorption cycle. Therefore, the excess heat available for exchange with the adsorber feed or the hydrogen purge gas also varies by as much as 50 percent over an adsorption cycle. Two separate embodiments of the invention overcome this problem. The first embodiment of the invention is one where the adsorber feed, the hydrogen purge gas, or both, are each first heat exchanged with the desorption effluent and then with a controlled variable heat-providing stream such as a steam or hot oil stream. The controlled variable steam or hot oil stream will either provide the balance of heat necessary for a constant inlet temperature to a fired heater or to increase the temperature of the adsorber feed, the hydrogen purge gas, or both, closer to the operating temperature of the adsorption zone. When the desorption effluent mass flow is low, the steam or hot oil stream is adjusted to provide a greater portion of the overall heat needed. When the desorption effluent mass flow is high, the steam or hot oil stream is adjusted to provide a lesser portion of the overall heat needed. In other words, the steam or hot oil stream is adjusted to maintain a constant outlet temperature from the heat exchanger of the adsorber feed, the hydrogen purge gas, or both. One steam or hot oil stream may be used for all exchanges, or when exchanging both the adsorber feed and the hydrogen purge gas, a separate steam or hot oil stream may be used for each. Even with the requirement of one or more controlled variable steam or hot oil streams to augment the temperature increase of the adsorber feed, the hydrogen purge gas, or both, the overall utility cost is reduced since the excess heat of the desorption effluent is conserved.

While heat exchange with a controlled variable hot oil stream is typically sufficient to heat the adsorber feed, the hydrogen purge gas, or both, to the temperature of the adsorption zone, heat exchange with the amount of steam usually available in a refinery setting may not be sufficient to achieve the temperature of the adsorption zone. In that case, a fired heater may also be used to bring the temperature of the streams to about that of the adsorption zone.

Another embodiment of the invention requires a surge drum to be placed on the desorption effluent line. The surge drum is a vessel for providing a constant space velocity or mass flow desorption effluent. The "constant" is meant herein to mean relatively constant, not absolutely constant, i.e., fluctuations of about 5 to about 10 percent are expected and are acceptable. The surge drum contains a volume or reservoir of the desorption effluent that varies over an adsorption cycle. The space velocity or mass flow of the desorption effluent entering the surge drum will vary by as much as 50 percent, but the space velocity or mass flow of the desorption effluent exiting the surge drum is relatively constant. The constant space velocity desorption effluent is then heat exchanged with the adsorber feed, the hydrogen purge gas, or both. Depending upon the relative operating temperatures of the isomerization reactor and the adsorption zone, additional heating of the adsorber feed, the hydrogen purge gas, or both, using traditional heaters may be required, but the overall utility requirement is reduced through the conservation of the excess heat in the desorption effluent.

Yet another embodiment of the invention is one where the adsorber feed, the hydrogen purge gas, or both, are heat exchanged one or more times with the reactor effluent in addition to being heat exchanged with the desorption effluent. The separation of the reactor effluent into the adsorber feed and the hydrogen purge gas takes place at a temperature lower than that of the reactor effluent, thereby providing excess heat available for exchange. The adsorber feed, the hydrogen purge gas, or both, may further be heat exchanged with the adsorption effluent from the adsorption zone.

Without intending any limitation on the scope of the present invention and as merely illustrative, this invention is explained below in specific terms as applied to one specific embodiment of the invention, the total isomerization of normal $C_5$ and $C_6$ hydrocarbons using a sulfated zirconia catalyst in an isomerization reactor, and a zeolitic molecular sieve adsorbent in an adsorption zone. For ease of understanding, the process of the invention described in detail below is limited to the adsorber-lead embodiment of the invention utilizing controlled variable steam streams for additional heat exchange followed by fired heaters.

Referring now to the figure, an adsorber-feed in line 32 and a fresh feed stream in line 2, both containing normal and non-normal $C_5$ and $C_6$ hydrocarbons, are combined to form a combined feed in line 42 that is introduced to adsorption zone 8. Prior to the combining, the fresh feed stream 2 is exchanged with an adsorption effluent stream 10 using heat exchanger 4 and then flowed to fired heater 6 in order to achieve the adsorption zone operating temperature of 260°

C. (500° F.). Hydrogen purge gas via line 54 is also introduced to adsorption zone 8. Adsorption zones in total isomerization processes are well known in the art, and the adsorption zone depicted in the figure is extremely simplified; individual beds and valving are not shown. In general terms, adsorption zone 8 is a four-bed zone operated at 260° C. (500° F.) and 250 psig and contains zeolitic molecular sieve adsorbent. Each bed in adsorption zone 8 cyclically undergoes A-1 adsorption fill, A-2 adsorption, D-1 void space purging and D-2 purge desorption as described above. The combined feed in line 42 is directed to those beds undergoing A-1 adsorption fill and A-2 adsorption. The hydrogen purge gas in line 54 is directed to those beds undergoing D-1 void space purging, and D-2 purge desorption. An adsorption effluent stream containing largely non-normal hydrocarbons in line 10 is removed from those beds undergoing A-2 adsorption and D-1 void space purging. After heat exchange with the fresh feed stream in line 2, the adsorption effluent is further cooled using cooling water exchanger 12 and conducted to separator drum 14 which is operated at from about 38° C. (100° F.) to about 66° C. (150° F.) and 200 psig where it is flashed and separated into a hydrogen-rich stream 18 and a hydrocarbon-rich stream 16. The hydrogen-rich stream is combined with the hydrogen purge gas stream 52 in order to conserve hydrogen. The hydrocarbon-rich stream 18 contains the desired isomerized product and may be flowed to a stabilizer to remove light gas and reduce the vapor pressure. A desorbent effluent containing largely normal hydrocarbons and some hydrogen is withdrawn via line 20 from those adsorption zone beds undergoing D-2 purge desorption. Because of the cyclical nature of the adsorption zone, the mass flow of the desorption effluent in line 20 will vary considerably, up to about 50 percent, depending upon the current state of the cycle. The desorption effluent exits the adsorption zone at a temperature of 260° C. (500° F.).

The desorption effluent in line 20 will be introduced to an isomerization reactor 22 that is operated at an outlet temperature of 176° C. (350° F.) and a pressure of 200 psig and contains a sulfated zirconia catalyst. Note that the desorption effluent exits adsorption zone 8 at a temperature of 260° C. (500° F.), but needs to be at a temperature of 149° C. (300° F.) to enter isomerization zone 22, note that the reactions in the isomerization zone are exothermal. To reduce the temperature of the desorption effluent in line 20 the desorption effluent is heat exchanged with adsorber feed in line 32 using heat exchanger 36 and/or with hydrogen purge gas in line 54 using heat exchanger 58. Excess heat is conserved providing a reduction in utility costs and, at the point of entry of isomerization reactor 22, the temperature of the desorption effluent in line 20 is about that of the operating temperature of the isomerization reactor 22. In isomerization reactor 22, a portion of the normal hydrocarbons in the desorption effluent are isomerized to form non-normal hydrocarbons, and the reactor effluent withdrawn from isomerization reactor 22 in line 24 contains normal and non-normal hydrocarbons in near equilibrium proportions and hydrogen.

Reactor effluent in line 24 may be heat exchanged against the adsorber feed in exchanger 26 as well as cooling water in exchanger 28 and is conducted to separator drum 30 which is operated at from about 38° C. (100° F.) to about 66° C. (150° F.) and from about 150 to about 180 psig where it is flashed and separated into an adsorber feed in line 32 and a hydrogen purge gas in line 52, both of which are recycled to adsorption zone 8. As they exit separator drum 30, the adsorber feed in line 32 and the hydrogen purge gas in line 52 are at a temperature of from about 38° C. (100° F.) to about 66° C. (150° F.), and each stream needs to be adjusted to a temperature of 260° C. (500° F.), the operating temperature of the adsorption zone. As described above, the adsorber feed in line 32 is pumped in equipment 34 and the hydrogen purge gas in line 52 is combined with the hydrogen-rich stream in line 18 and compressed in equipment 56 and the combined stream is heat exchanged with the desorption effluent in line 20. However, the mass flow of the desorption effluent in line 20 varies considerably and therefore the amount of heat available for exchange varies considerably. To provide the additional variable balance of heat required so that the adsorber feed in line 32 and the hydrogen purge gas in line 54 are at the proper temperature, controlled variable steam exchangers are used. The partially-heated adsorber feed in line 32 is conducted to heat exchanger 38. The amount of steam that flows to heat exchanger 38 is controlled so as to provide only the balance of heat needed to bring the partially-heated adsorber feed to a constant outlet temperature which is then introduced to fired heater 40 thereby bringing the temperature in line 32 to the operating temperature of adsorption zone 8. Similarly, the partially-heated hydrogen purge gas in line 54 is conducted to heat exchanger 60. The amount of steam that flows to heat exchanger 60 is controlled so as to provide a constant outlet temperature which is then introduced to fired heater 62 thereby bringing the temperature in line 54 to the operating temperature of adsorption zone 8. The fully-heated adsorber feed in line 32, combined with the fresh feed stream to form combined stream 42, and the fully-heated hydrogen purge gas in line 54 are then introduced to the adsorption zone 8.

Alternately, a surge drum (not shown) may be located on the desorption effluent in line 20 at a point upstream of heat exchangers 36 and 58. The surge drum acts as a variable volume reservoir of desorption effluent so that the desorption effluent in line 20 that is downstream of the surge drum has only minor mass flow variations as compared to the up to 50 percent variations possible without the surge drum. When using a surge drum to eliminate the extreme variations in the mass flow of the desorption effluent in line 20, both heat exchangers 38 and 60 may be eliminated from the process.

It must be emphasized that the above description is merely illustrative of one embodiment and not intended as an undue limitation of the generally broad scope of the invention. Moreover, while the description is narrow in scope, one skilled in the art will understand how to extrapolate to the broader scope of the invention. For example, a reactor-lead flowscheme using the controlled variable steam streams and the heat exchangers used in conjunction with the controlled variable steam streams or a reactor-lead flow scheme using the surge drum on the desorption effluent can be readily extrapolated from the foregoing description. Furthermore, conserving the excess heat in the desorption effluent through heat exchange with only the adsorber feed or only the hydrogen purge gas, heat exchanging the adsorber feed, the hydrogen purge gas, or both, one or more times with the reactor effluent, and using a controlled variable hot oil stream in lieu of the controlled variable stream would be readily apparent to one skilled in the art.

What is claimed is:

1. A process for the isomerization of normal hydrocarbons in a stream containing mixed normal and non-normal hydrocarbons comprising:

a) heat exchanging a hydrocarbon-enriched stream, a hydrogen-enriched stream, or both, separately, with a variable mass flow desorption effluent so that the variable mass flow desorption effluent flowing into a reactor containing an isomerization catalyst is at about the operating temperature of the reactor, about 232° C. (450° F.) or less;

b) heat exchanging the hydrocarbon-enriched stream, the hydrogen-enriched stream, or both, separately, with at least one controlled variable heat providing stream so that the temperature of the hydrocarbon-enriched stream, the hydrogen-enriched stream or both, approaches the operating temperature of an adsorption zone, about 260° C. (500° F.) or greater, said adsorption zone containing an adsorbent having a selectivity for the normal hydrocarbons;

c) flowing the hydrocarbon-enriched stream to the adsorption zone to adsorb the normal hydrocarbons and collect the non-normal hydrocarbons; and d) desorbing the normal hydrocarbons from the adsorption zone using the hydrogen-enriched stream to produce the variable mass flow desorption effluent.

2. The process of claim 1 wherein the controlled variable heat providing stream is selected from the group consisting of a steam stream and a hot oil stream.

3. The process of claim 1 further comprising heat exchanging the hydrocarbon-enriched stream, the hydrogen-enriched stream or both, separately, with an effluent from the reactor.

4. The process of claim 1 further characterized in that in step (b) after the hydrocarbon-enriched stream, the hydrogen-enriched stream, or both, are heat exchanged, said hydrocarbon-enriched stream, the hydrogen-enriched stream, or both are further heated using a fired heater so that the temperatures of the hydrocarbon-enriched stream, the hydrogen-enriched stream or both, are at the operating temperature of the adsorption zone.

5. The process of claim 1 wherein the catalyst is sulfated zirconia.

6. The process of claim 1 wherein the adsorbent is zeolitic molecular sieve.

7. A process for the isomerization of normal hydrocarbons in a feed stream containing mixed normal and non-normal hydrocarbons comprising:

a) flowing the feed stream to a reactor containing an isomerization catalyst and operating at about 232° C. (450° F.) or less, or to an adsorption zone containing an adsorbent having a selectivity for the normal hydrocarbons and operating at about 260° C. (500° F.) or greater;

b) flowing a variable mass flow desorption effluent containing at least hydrogen and normal hydrocarbons to the reactor to form a reactor effluent containing hydrogen, normal hydrocarbons, and isomerized non-normal hydrocarbons;

c) separating the reactor effluent into a hydrogen-enriched stream and a hydrocarbon-enriched stream;

d) heat exchanging the hydrocarbon-enriched stream, the hydrogen-enriched stream, or both separately, with the variable mass flow desorption effluent so that the variable mass flow desorption effluent flowing into the reactor is at about the operating temperature of the reactor;

e) heat exchanging the hydrocarbon-enriched stream, the hydrogen-enriched stream, or both, with at least one controlled variable heat providing stream so that the temperature of the hydrocarbon-enriched stream, the hydrogen-enriched stream or both, approaches the operating temperature of the adsorption zone;

f) flowing the hydrocarbon-enriched stream to the adsorption zone to adsorb the normal hydrocarbons and collect the non-normal hydrocarbons; and g) desorbing the normal hydrocarbons from the adsorption zone using the hydrogen-enriched stream to produce the variable mass flow desorption effluent.

8. The process of claim 7 wherein the controlled variable heat providing stream is selected from the group consisting of a steam stream and a hot oil stream.

9. The process of claim 7 further comprising heat exchanging the hydrocarbon-enriched stream, the hydrogen-enriched stream or both, with the reactor effluent.

10. The process of claim 7 wherein the separation of the reactor effluent in step (c) is performed by flashing in a separator drum.

11. The process of claim 7 further characterized in that in step (e) after the hydrocarbon-enriched stream, the hydrogen-enriched stream, or both, are heat exchanged, said hydrocarbon-enriched stream, the hydrogen-enriched stream, or both, are further heated using a fired heater so that the temperatures of the hydrocarbon-enriched stream, the hydrogen-enriched stream or both, are at about the operating temperature of the adsorption zone.

12. The process of claim 7 wherein the catalyst is sulfated zirconia.

13. The process of claim 7 wherein the adsorbent is zeolitic molecular sieve.

14. A process for the isomerization of normal hydrocarbons in a stream containing mixed normal and non-normal hydrocarbons comprising:

a) heat exchanging a hydrocarbon-enriched stream, a hydrogen-enriched stream, or both, separately, with a constant mass flow desorption effluent so that the constant mass flow desorption effluent flowing into a reactor containing an isomerization catalyst is at about the operating temperature of the reactor, about 232° C. (450° F.) or less;

b) flowing the hydrocarbon-enriched stream to an adsorption zone having a selectivity for the normal hydrocarbons and operating at about 260° C. (500° F.) or greater, to adsorb the normal hydrocarbons and collect the non-normal hydrocarbons;

c) desorbing the normal hydrocarbons from the adsorption zone using the hydrogen-enriched stream to produce a variable mass flow desorption effluent; and d) flowing the variable mass flow desorption effluent to a surge drum to provide the constant mass flow desorption effluent.

15. The process of claim 14 further characterized in that in step (a) after heat exchanging the hydrocarbon-enriched stream, the hydrogen-enriched stream, or both, said hydrocarbon-enriched stream, hydrogen-enriched stream, or both, are further heated using a fired heater so that the hydrocarbon-enriched stream, the hydrogen-enriched stream or both, flowing into the adsorption zone are at about the operating temperature of the adsorption zone.

16. The process of claim 14 further comprising heat exchanging the hydrocarbon-enriched stream, the hydrogen-enriched stream or both, separately, with the reactor effluent.

17. The process of claim 14 wherein the catalyst is sulfated zirconia.

18. The process of claim 14 wherein the adsorbent is zeolitic molecular sieve.

19. A process for the isomerization of normal hydrocarbons in a feed stream containing mixed normal and non-normal hydrocarbons comprising:

a) flowing the feed stream to a reactor containing an isomerization catalyst and operating at about 232° C. (450° F.) or less, or to an adsorption zone containing an adsorbent having a selectivity for the normal hydrocarbons and operating at about 260° C. (500° F.) or greater;

b) flowing a constant mass flow desorption effluent containing at least hydrogen and normal hydrocarbons to the reactor to form a reactor effluent containing hydrogen, normal hydrocarbons, and isomerized non-normal hydrocarbons;

c) separating the reactor effluent into a hydrogen-enriched stream and a hydrocarbon-enriched stream;

d) heat exchanging the hydrocarbon-enriched stream, the hydrogen-enriched stream, or both, with the constant mass flow desorption effluent so that the constant mass flow desorption effluent flowing into the reactor is at about the operating temperature of the reactor;

e) flowing the hydrocarbon-enriched stream to the adsorption zone, to adsorb the normal hydrocarbons and collect the non-normal hydrocarbons;

f) desorbing the normal hydrocarbons from the adsorption zone using the hydrogen-enriched stream to produce a variable mass flow desorption effluent; and g) flowing the variable mass flow desorption effluent to a surge drum to provide the constant mass flow desorption effluent.

20. The process of claim 19 further characterized in that in step (d) after the hydrocarbon-enriched stream, the hydrogen-enriched stream, or both, are heat exchanged, said hydrocarbon-enriched stream, hydrogen-enriched stream, or both are further heated using a fired heater so that the hydrocarbon-enriched stream, the hydrogen-enriched stream or both, flowing into the adsorption zone are at about the operating temperature of the adsorption zone.

21. The process of claim 19 further comprising heat exchanging the hydrocarbon-enriched stream, the hydrogen-enriched stream or both, with the reactor effluent.

22. The process of claim 19 wherein the separation of the reactor effluent in step (c) is performed by flashing in a separator drum.

23. The process of claim 19 wherein the catalyst is sulfated zirconia.

24. The process of claim 19 wherein the adsorbent is zeolitic molecular sieve.

* * * * *